US006063372A

United States Patent [19]
Banchereau et al.

[11] Patent Number: 6,063,372
[45] Date of Patent: May 16, 2000

[54] USES OF MAMMALIAN CTLA-8 AND RELATED REAGENTS

[75] Inventors: Jacques Banchereau, Dallas, Tex.; Odile Djossou, Francheville, France; Leopoldo Flores-Romo, Houston, Tex.; Francois Fossiez, Marcy L'Etoile; Pierre Golstein, Marseille, both of France; Mala Krishna, Los Altos, Calif.; Serge J. E. Lebecque, Civrieux, France; Richard Murray, Mountain View, Calif.

[73] Assignees: Inserm, Institut National de la Sante et de la Recherche Medicale, Paris, France; Schering Corporation, Kenilworth, N.J.; Schering-Plough, Levallois-Perret, France

[21] Appl. No.: 08/736,299

[22] Filed: Oct. 24, 1996

Related U.S. Application Data
[60] Provisional application No. 60/005,909, Oct. 27, 1995.

[51] Int. Cl.$^7$ .................................................. A61K 45/05
[52] U.S. Cl. ........................ 424/85.2; 424/85.1; 530/351
[58] Field of Search .......................... 530/351; 424/85.1, 424/85.2

[56] References Cited

FOREIGN PATENT DOCUMENTS

| WO 91/07988 | 6/1991 | WIPO . |
| WO 92/03151 | 3/1992 | WIPO . |
| WO 95/16458 | 6/1995 | WIPO . |
| WO95/18826 | 7/1995 | WIPO . |

OTHER PUBLICATIONS

Arthur M. Cohen, et al., *Infection and Immunity*, 56(11):2861–2865, Nov. 1988. "In Vivo Activation of Neutrophil Funtion in Hamsters by Recombinant Human Granulocyte Colony–Stimulating Factor".

F. Fossiez, et al., *9th International Congress of Immunology, San Francisco, CA, Jul. 23–29, 1995*, p. 544, see abstract No. 3222. "Human CTLA8: A Novel Cytokine With Proinflammatory Activities".

M. Krishna, et al., *37th Annual Meeting of the American Society of Hematology, Seattle Washington, USA, Dec. 1–5, 1995*. Blood, 86(10 Suppl. 1):abstract 1988, Dec. 1995. A Novel Cytokine, CTLA–8 Induces Peripheral Blood Neutrophilia and Protection from Lethal Bacterial Infection in Mice.

Jens–Christian Albrecht, et al., *Journal of Virology*, vol. 66, No. 8, pp. 5047–5058, Aug. 1992. "Primary Structure of the Herpesvirus Saimiri Genome".

Jens–Christian Albrecht, et al., *Virology*, vol. 174, pp. 533–542, 1990. "Structural Organization of the Conserved Gene Block of *Herpesvirus saimiri* Coding for DNA Polymerases, Glycoprotein B, and Major DNA Binding Protein".

D. Caput, et al., *Proc. Nat'l. Acad. Sci.*, vol. 83, pp. 1670–1674, Mar. 1986. "Identification of a common nucleotide sequence in the 3'–untranslated region of mRNA moleculors specifying inflammatory mediates".

Marilyn Kozak, *The Journal of Cell Biology*, vol. 115, No. 4, pp. 887–903, Nov. 1991. "An analysis of Vertebrate mRNA sequences: Intimations of Translational Control".

Marilyn Kozak, *J. Biol. Chem.*, vol. 266, No. 30, pp. 19867–19870, Oct. 1991. "Structural Features in Eukaryotic mRNAs that Modulate the Initiation of Translation".

John Nicholas, et al., *Virology*, vol. 179, pp. 189–200, 1990. "Gene Expression in Cells Infected with Gammaherpes–virus Saimiri: Properties of Transcripts from Two Immediate–Early Genes".

John Nicholas, et al., Gen Bank Accession No. M60286, pp. 1–3, Mar. 1991.

Marc Piechaczyk, et al., *Gene*, vol. 72, pp. 287–295, 1988. "Role of RNA Structures in c–myc and c–fos Gene Regulations".

Eric Rouvier, et al., *The Journal of Immunology*, vol. 150, No. 12, pp. 5445–5456, Jun. 1993. "CTLA–8, Cloned from an Activated T Cell, Bearing AU–Rich Messenger RNA Instability Sequences, and Homologous to a Herpesvirus Saimiri Gene".

Eric Rouvier, et al., Gen Black Accession No. L13839, pp. 1–2, Apr. 1993.

Eric Rouvier, et al., Abstract and poster presented at the International Congress of Immunology, Budapest, Hungary: abstract and poster panels, Aug. 1992. "A Search for Novel Molecules Differentially Expressed in Cytotoxic T Cells".

Gary Shaw, et al., *Cell*, vol. 46, pp. 659–667, Aug. 1986. "A Conserved AU Sequence from the 3'Untranslated Region of GM–CSF mRNA Mediates Selective mRNA Degradation".

Johnson, et al., *Proc. Nat'l Acad. Sci.* vol. 74, No. 9, pp. 3879–3884, 1977. "Pure and Mixed Erythroid Colony Formation In Vitro Stimulated by Spleen Conditioned Medium with no Detectable Erythropoietin".

A. Neil Barclay, et al., Academic Press, pp. 290–291, 1993. "The Leucocyte Antigen FactsBook".

Hyun Soon Lillehoj, et al. *Eur. J. Immunol.* vol. 18, pp. 2059–2065, 1988. "Functional and Biochemical Characterizations of Avian T Lymphocyte Antigens Identified by Monoclonal Antibodies,".

Sabine Muller, et al., *Eur. J. Immunol.* vol. 25, pp. 1744–1748, 1995. "Cloning of ATAC, an Activation–Induced, Chemokine–Related Molecule Exclusively Expressed in CD8+ T Lymphocytes".

Zhengbin Yao, et al., *J. of Immunol.*, vol. 155, pp. 5483–5486, 1995. "Human IL–17: A Novel Cytokine Derived from T Cells".

*Primary Examiner*—Christina Y. Chan
*Assistant Examiner*—Patrick J. Nolan
*Attorney, Agent, or Firm*—Edwin P. Ching

[57] ABSTRACT

Compositions and methods for using CTLA-8 to treat an abnormal physiological condition in an individual. The methods comprise administering a therapeutically effective amount of CTLA-8 alone, or in combination with other therapeutic reagents; or a CTLA-8 antagonist.

15 Claims, No Drawings

USES OF MAMMALIAN CTLA-8 AND RELATED REAGENTS

The present application hereby incorporates by reference U.S. Ser. Nos. 08/250,846, filed May 27, 1994 now pending; 08/177,747, filed Jan. 5, 1994 now abandoned; and 08/077,203, filed Jun. 14, 1993 now abandoned. Also incorporated by reference is PCT/US95/00001, filed Jan. 3, 1995. This application is a conversion from a provisional U.S. patent application, filed Oct. 27, 1995, assigned number 60/005,909, to a regular U.S. patent application.

FIELD OF THE INVENTION

The present invention relates to methods of using proteins which function in controlling physiology, development, and differentiation of mammalian cells, e.g., cells of a mammalian immune system. In particular, it provides methods of using proteins and mimetics which regulate cellular physiology, development, differentiation, or function of various cell types, including hematopoietic cells.

BACKGROUND OF THE INVENTION

The immune system of vertebrates consists of a number of organs and several different cell types. Two major cell types include the myeloid and lymphoid lineages. Among the lymphoid cell lineage are B cells, which were originally characterized as differentiating in fetal liver or adult bone marrow, and T cells, which were originally characterized as differentiating in the thymus. See, e.g., Paul (ed.) (1993) *Fundamental Immunology* (3d ed.) Raven Press, New York.

In many aspects of the development of an immune response or cellular differentiation, soluble proteins known as cytokines play a critical role in regulating cellular interactions. These cytokines also mediate cellular activities in many ways. They have been shown, in many cases, to modulate proliferation, growth, and differentiation of hematopoietic stem cells into the vast number of progenitors composing the lineages responsible for an immune response. They are also quite important in immunological responses and physiology.

However, the cellular molecules which are expressed by different developmental stages of cells in these maturation pathways are still incompletely identified. Moreover, the roles and mechanisms of action of signaling molecules which induce, sustain, or modulate the various physiological, developmental, or proliferative states of these cells is poorly understood. Clearly, the immune system and its response to various stresses has relevance to medicine, e.g., infectious diseases, cancer related responses and treatment, allergic and transplantation rejection responses. See, e.g., Thorn, et al. *Harrison's Principles of Internal Medicine* McGraw/Hill, New York.

Medical science relies, in large degree, to appropriate recruitment or suppression of the immune system in effecting cures for insufficient or improper physiological responses to environmental factors. However, the lack of understanding of how the immune system is regulated or differentiates has blocked the ability to advantageously modulate the immunological mechanisms to biological challenges, i.e., bacterial, fungal, or viral. Medical conditions characterized by abnormal or inappropriate regulation of the development or physiology of relevant cells thus remain unmanageable. The discovery and characterization of specific cytokines and their physiological effects will contribute to the development of therapies for a broad range of degenerative or other conditions which affect the immune system, hematopoietic cells, as well as other cell types. The present invention provides solutions to some of these and many other problems.

SUMMARY OF THE INVENTION

The present invention is based, in part, upon the discovery of the physiological role of CTLA-8 in various models of immune response. In particular, the role of CTLA-8 has been elucidated in pathways involved in infectious disease, hematopoietic development, and viral infection.

The present invention embraces a composition comprising mammalian G-CSF, and CTLA-8 and/or IL-6. Preferably, G-CSF, CTLA-8, and IL-6 are recombinant human proteins. A pharmaceutical composition comprising an acceptable carrier is also contemplated.

The present invention also provides a method of administering the composition in order to treat an animal suffering from, e.g., a microbial infection; sepsis; or abnormal hematopoiesis. Also embraced is a method of administering CTLA-8 alone to treat, e.g., a microbial infection; sepsis; or abnormal hematopoiesis. In particular embodiments, the CTLA-8 increases the level of neutrophils in the peripheral blood and/or induces the differentiation of a CD34+ precursor cell to a neutrophil or monocyte cell.

The invention includes a method of administering an effective amount of CTLA-8 to protect an animal from a gram negative bacterial infection, e.g., sepsis, resulting from a thoracic or abdominal surgical procedure. Also embraced is a method of administering CTLA-8, e.g., before cytoablative therapy; thoracic surgery; or abdominal surgery.

DETAILED DESCRIPTION OF THE PREFERRED EMBODIMENTS

OUTLINE

I. General

II. Nucleic Acids

A. natural isolates; methods

B. synthetic genes

C. methods to isolate

III. Purified CTLA-8 protein

A. physical properties

B. biological properties

IV. Making CTLA-8 protein; Mimetics

A. recombinant methods

B. synthetic methods

C. natural purification

V. Physical Variants

A. sequence variants, fragments

B. post-translational variants 1. glycosylation 2. others

VI. Functional Variants

A. analogs; fragments 1. agonists 2. antagonists

B. mimetics 1. protein 2. chemicals

C. species variants
VII. Antibodies
 A. polyclonal
 B. monoclonal
 C. fragments, binding compositions
VIII. Uses
 A. diagnostic
 B. therapeutic
IX. Kits
 A. nucleic acid reagents
 B. protein reagents
 C. antibody reagents I. General The present invention makes use of DNA sequence encoding various mammalian proteins which exhibit properties characteristic of functionally significant T cell expressed molecules. The cDNA sequence exhibits various features which are characteristic of mRNAs encoding cytokines, growth factors, and oncogenes. A murine gene originally thought to be from a mouse, but now recognized as rat as described herein, contains an open reading frame encoding a putative 150 amino acid protein. This protein is 57% homologous to a putative protein encoded by a viral genome, the herpesvirus Saimiri ORF13. The message was isolated using a subtraction hybridization method applied to T cells.

These proteins are designated CTLA-8 proteins. The natural proteins should be capable of mediating various physiological responses which would lead to biological or physiological responses in target cells. Initial studies had localized the message encoding this protein to various cell lines of hematopoietic cells. Genes encoding the antigen have been mapped to mouse chromosome 1A and human chromosome 2q31. The original characterization of murine CTLA-8 (rat) was reported by Rouvier, et al. (1993) *J. Immunol.* 150:5445–5456. Similar sequences for proteins in other mammalian species should also be available, particularly mouse and human. See, U.S. Ser. Nos. 08/250,846 now pending; 08/177,747 now abandoned; and 08/077,203 now abandoned.

Culturing adherent human synovial cells with CTLA-8 results in the production IL-6 and IL-8. Certain bacterial challenges to mice are accepted models for septic conditions. Administration of recombinant IL-6 to IL-6 knockout mice confers a profound protective effect during bacterial challenge. Thus CTLA-8 is an important factor in the induction of this IL-6 mediated protection. Resistance to several common types of bacterial infections is also heavily dependent on the presence of neutrophils. Pretreatment of animals with CTLA-8, which is able to induce neutrophilia, are completely protected from lethal *E. coli* infection. G-CSF induces the release of neutrophils from the bone marrow to the periphery but with a relatively slow effect, e.g., over days. Moreover, a significant number of patients who receive bone-marrow transplants following cyto-ablative therapy are refractive to G-CSF peripheral blood mobilization. CTLA-8 and IL-6 on the other hand, stimulate the release of neutrophils from the peripheral epithelium into the circulation. This is a much faster effect, e.g., over hours.

The mobilization of neutrophils by the CTLA-8/IL-6 pathway is more immediate, which is clearly beneficial in disease states requiring fast amelioration. For example, some patients undergoing surgery, i.e., thoracic or abdominal, will suffer a post-operative septic crisis caused by an infection by, or clearance of, a gram negative bacteria. Berkow (ed.) *The Merck Manual of Diagnosis and Therapy*, Merck & Co., Rahway, N.J. Treatment must be aggressive and the results must be immediate, e.g., within hours, in order to avoid septic shock. A combination therapy of CTLA-8 and G-CSF, IL-6 and G-CSF, or CTLA-8 alone may provide this immediate cure. These combinations may also be useful in conferring protection against infection or sepsis by pre-treating an individual undergoing cyto-ablative or surgical therapies, perhaps days before the procedure is actually performed.

CTLA-8 is also able to induce the secretion of Granulocyte Colony Stimulating Factor (G-CSF) by rheumatoid synoviocytes and kidney carcinoma epithelial cell line, suggestive of a role in hematopoiesis. CTLA-8 has a striking effect on the proliferation and differentiation of CD34+ precursor cells into predominately neutrophil populations based on morphology and expression patterns of surface antigens. Patients receiving cyto-ablative therapy for the treatment of cancer are often dose limited by the extent of the resulting neutropenia, which can render these patients susceptible to microbial infection, i.e., bacterial or fungal. Thus a combination of CTLA-8 and G-CSF, or IL-6 and G-CSF, may accelerate effective re-population of hematopoietic cells. The combination should have an effect greater than either alone, as the effects appear to be mediated via different pathways.

As a general activator of cytokine secretion by fibroblasts, CTLA-8 is likely to enhance the secretion of fibroblast IFN-$\beta$. This may therefore result in the development of an antiviral state that will limit viral infections.

The descriptions below are directed, for exemplary purposes, to a murine (rat or mouse) or human CTLA-8 protein, but are likewise applicable to related embodiments from other species.

II. Nucleic Acids

General description of nucleic acids, their manipulation, and their uses are provided in the following references: U.S. Ser. Nos. 08/250,846 now pending; 08/177,747 now abandoned; 08/077,203 now abandoned; PCT/US95/00001; Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; Rosenberg (1992) *J. Clinical Oncology* 10:180–199; and Cournoyer and Caskey (1993) *Ann. Rev. Immunol.* 11:297–329; Wetmur and Davidson (1968)*J. Mol. Biol.* 31:349–370; each of which are incorporated by reference. Additional aspects will be apparent to a person having ordinary skill in the art in light of the teachings provided herein.

III. Purified CTLA-8 protein

General descriptions of proteins and polypeptides in pharmaceutical or biochemical contexts can be found, e.g., in: Goodman, et al. (eds.) (1990) *Goodman & Gilman's: The Pharmacological Bases of Therapeutics* (8th ed.), Pergamon Press; Freifelder (1982) Physical Biochemistry (2d ed.), W. H. Freeman; Cantor and Schimmel (1980) Biophysical Chemistry, parts 1–3, W. H. Freeman & Co., San Francisco. Specific descriptions of rat, mouse, and human CTLA-8 are found, e.g., in Rouvier, et al. (1993) *J. Immunol.* 150:5445–5456; U.S. Ser. Nos. 08/250,846; 35 08/177,747; 08/077,203; and PCT/US95/00001.

IV. Making CTLA-8 protein; Mimetics

DNA which encodes the CTLA-8 protein or fragments thereof can be obtained by chemical synthesis, screening cDNA libraries, or by screening genomic libraries prepared from a wide variety of cell lines or tissue samples.

This DNA can be expressed in a wide variety of expression systems as described in, e.g., U.S. Ser. Nos. 08/250,846 now pending; 08/177,747 now abandoned; 08/077,203 now abandoned; PCT/US95/00001; Kaufman, et al. (1985) *Molec. and Cell. Biol.* 5:1750–1759; Pouwels, et al. (1985 and Supplements) *Cloning Vectors: A Laboratory Manual,* Elsevier, N.Y., Rodriquez, et al. (1988) (eds.) *Vectors: A Survey of Molecular Cloning Vectors and Their Uses,* Buttersworth, Boston, Mass.; Rodriguez and Denhardt (eds.) *Vectors: A Survey of Molecular Cloning Vectors and Their Uses,* Buttersworth, Boston, Chapter 10, pp. 205–236; Okayama, et al. (1985) *Mol. Cell Biol.* 5:1136–1142; pMC1neo Poly-A, see Thomas, et al. (1987) *Cell* 51:503–512; O'Reilly, et al. (1992) *Baculovirus Expression Vectors: A Laboratory Manual* Freeman and Co., CRC Press, Boca Raton, Fla.; Low (1989) *Biochim. Biophys. Acta* 988:427–454; Tse, et al. (1985) *Science* 230:1003–1008; and Brunner, et al. (1991) *J. Cell Biol.* 114:1275–1283; each of which is incorporated by reference.

Now that the CTLA-8 protein has been characterized, fragments or derivatives thereof can be prepared by conventional processes for synthesizing peptides. These include processes such as are described in Stewart and Young (1984) *Solid Phase Peptide Synthesis,* Pierce Chemical Co., Rockford, Ill.; Bodanszky and Bodanszky (1984) *The Practice of Peptide Synthesis, Springer-Verlag, New York;* Bodanszky (1984) *The Principles of Peptide Synthesis,* Springer-Verlag, New York; and Merrifield, et al. (1963) in *J. Am. Chem. Soc.* 85:2149–2156; each of which is incorporated by reference. Additional aspects will be apparent to a person having ordinary skill in the art in light of the teaching provided herein.

V. Physical Variants

Proteins or peptides having substantial amino acid sequence homology with the amino acid sequence of the CTLA-8 protein are also contemplated. The variants include species or allelic variants. Homology, or sequence identity is defined in , e.g., U.S. Ser. Nos. 08/250,846 now pending; 08/177,747 now abandoned; 08/077,203 now abandoned; PCT/US95/00001; Needleham, et al. (1970) *J. Mol. Biol.* 48:443–453; Sankoff, et al. (1983) Chapter One in *Time Warps. String Edits, and Macromolecules: The Theory and Practice of Sequence Comparison* Addison-Wesley, Reading, Mass.; software packages from IntelliGenetics, Mountain View, Calif.; and the University of Wisconsin Genetics Computer Group, Madison, Wis.

The isolated DNA encoding a CTLA-8 protein can be readily modified as described in, e.g., U.S. Ser. Nos. 08/250, 846; 08/177,747; 08/077,203; PCT/US95/00001; Sambrook, et al. (1989) and Ausubel, et al. (1987 and Supplements); Cunningham, et al. (1989) *Science* 243:1330–1336; O'Dowd, et al. (1988) *J. Biol. Chem.* 263:15985–15992; and Carruthers (1981) *Tetra. Letts.* 22:1859–1862; each of which are incorporated by reference. Additional methods will be apparent to a person having ordinary skill in the art in light of the teachings provided herein.

VI. Functional Variants

The blocking of physiological response to CTLA-8 proteins may result from the inhibition of binding of the antigen to its natural binding partner by a variant of natural CTLA-8 Methods for making such a variant are described in, e.g., U.S. Ser. Nos. 08/250,846 now pending; 08/177,747 now abandoned; 08/077,203 now abandoned; PCT/US95/00001; Godowski, et al. (1988) *Science* 241:812–816; Beaucage and Carruthers (1981) *Tetra. Letts.* 22:1859–1862; Sambrook, et al. (1989) *Molecular Cloning: A Laboratory Manual* (2d ed.), Vols. 1–3, Cold Spring Harbor Laboratory; Merrifield (1963) *J. Amer. Chem. Soc.* 85:2149–2156; Merrifield (1986) *Science* 232: 341–347; Atherton, et al. (1989) *Solid Phase Peptide Synthesis: A Practical Approach,* IRL Press, Oxford; Cunningham, et al. (1989) *Science* 243:1339–1336; O'Dowd, et al. (1988) *J. Biol. Chem.* 263:15985–15992; and Lechleiter, et al. (1990) *EMBO J.* 9:4381–4390; each of which is incorporated by reference. Additional methods will be apparent to a person having ordinary skill in the art in light of the teachings provided herein.

VII. Antibodies

Antibodies can be raised to the various CTLA-8 proteins, including species or allelic variants, and fragments thereof, both in their naturally occurring forms and in their recombinant forms. Additionally, antibodies can be raised to CTLA-8 proteins in either their active forms or in their inactive forms. Anti-idiotypic antibodies are also contemplated. Methods for generating antibodies and binding compositions and their uses are described in, e.g., U.S. Ser. Nos. 08/250,846 now pending; 08/177,747 now abandoned; 08/077,203 now abandoned; PCT/US95/00001; Coligan (1991) *Current Protocols in Immunology* Wiley/Greene; Harlow and Lane (1989) *Antibodies: A Laboratory Manual* Cold Spring Harbor Press; Chan (ed.) (1987) *Immunoassay: A Practical Guide* Academic Press, Orlando, Fla.; Ngo (ed.) (1988) *Nonisotopic Immunoassay* Plenum Press, NY; Price and Newman (eds.) (1991) *Principles and Practice of Immunoassay* Stockton Press, NY; *Microbiology,* Hoeber Medical Division, Harper and Row, 1969; Landsteiner (1962) *Specificity of Serological Reactions,* Dover Publications, New York, Williams, et al. (1967) *Methods in Immunology and Immunochemistry,* Vol. 1, Academic Press, New York; Stites, et al. (eds.) *Basic and Clinical Immunology* (4th ed.), Lange Medical Publications, Los Altos, Calif., and references cited therein; Harlow and Lane (1988) *Antibodies: A Laboratory Manual,* CSH Press; Goding (1986) *Monoclonal Antibodies: Principles and Practice* (2d ed.) Academic Press, New York; Kohler and Milstein (1975) in *Nature* 256: 495–497; Huse, et al. (1989) "Generation of a Large Combinatorial Library of the Immunoglobulin Repertoire in Phage Lambda" *Science* 246:1275–1281; Ward, et al. (1989) *Nature* 341:544–546; U.S. Pat. Nos. 3,817,837; 3,850,752; 3,939,350; 3,996,345; 4,277,437; 4,275,149; and 4,366,241; and Cabilly, U.S. Pat. No. 4,816,567; each of which is incorporated by reference. Additional methods will be apparent to a person having ordinary skill in the art in light of the teachings provided herein.

VIII. Uses

Mammalian CTLA-8 will have a variety of therapeutic uses for, i.e., the treatment of septicemia; hematopoietic development; or the treatment of viral conditions. Administration of an effective amount of CTLA-8 will typically be at least about 100 ng per kg of body weight; usually at least about 1 $\mu$g per kg of body weight; and often less than about 1 mg per kg of body weight; or preferably less than about 10 mg per kg of body weight. An effective amount will decrease the symptoms typically by at least about 10%; usually by at least about 20%; preferably at least about 30%; or more preferably at least about 50%. The present invention provides reagents which will find use in additional diagnostic and therapeutic applications as described elsewhere herein, e.g., in the general description for physiological or developmental abnormalities, or below in the description of kits for diagnosis. See, e.g., U.S. Ser. Nos. 08/250,846 now pending; 08/177,747 now abandoned; 08/077,203 now abandoned; PCT/US95/00001; Berkow (ed.) *The Merck Manual of Diagnosis and Therapy,* Merck & Co., Rahway, N.J.; Thorn, et al. *Harrison's Principles of Internal Medicine,* McGraw-Hill, NY; Gilman, et al. (eds.) (1990) *Goodman and Gilman's: The Pharmacological Bases of Therapeutics,* 8th Ed., Pergamon Press; Remington's Pharmaceutical Sciences, 17th ed. (1990), Mack Publishing Co., Easton, Penn; Langer (1990) *Science* 249:1527–1533; *Merck Index,* Merck & Co., Rahway, N.J.; Avis, et al. (eds.) (1993) *Pharmaceutical Dosage Forms: Parenteral Medications* 2d ed., Dekker, N.Y.; Lieberman, et al. (eds.) (1990) *Pharmaceutical Dosage Forms: Tablets* 2d ed., Dekker, N.Y.; Lieberman, et al. (eds.) (1990) *Pharmaceutical Dosage Forms: Disperse Systems* Dekker, N.Y.; Fodor, et al. (1991) *Science* 251:767–773, Coligan *Current Protocols in Immunology;* Hood, et al. *Immunology* Benjamin/Cummings; Paul (ed.) *Fundamental Immunology; Methods in Enzymology* Academic Press; Parce, et al. (1989) *Science* 246:243–247; Owicki, et al. (1990) *Proc. Nat'l Acad. Sci. USA* 87:4007–4011; and Blundell and Johnson (1976) *Protein Crystallography,* Academic Press, New York; each of which is incorporated by reference. Additional uses will be apparent to a person having ordinary skill in the art in light of the teachings provided herein.

IX. Kits

This invention also contemplates use of CTLA-8 proteins, fragments thereof, peptides, and their fusion products may also be used in a variety of diagnostic kits and methods for detecting the presence of a binding composition as described in, e.g., U.S. Ser. Nos. 08/250,846 now pending; 08/177,747 now abandoned; 08/077,203 now abandoned; PCT/US95/00001; Harlow and Lane (1988) *Antibodies: A Laboratory Manual,* CSH; U.S. Pat. Nos. 3,645,090; 3,940,475; Rattle, et al. (1984) *Clin. Chem.* 30:1457–1461; 4,659,678; and Viallet, et al. (1989) *Progress in Growth Factor Res.* 1:89–97; each of which is incorporated by reference.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual,* (2d ed.), vols. 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene/Wiley, New York; Innis, et al. (eds.) (1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology,* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation of a DNA clone encoding CTLA-8 protein

Isolation of murine CTLA-8 is described in Rouvier, et al. (1993) *J. Immunol.* 150:5445–5456. See also U.S. Ser. No. 08/077,203 now abandoned.

Source of the CTLA-8 message

Various cell lines are screened using an appropriate probe for high level message expression. Appropriate cell lines are selected based upon expression levels of the CTLA-8 message. Applicants used subtractive hybridization methods on activated cytotoxic T cells.

Isolation of a CTLA-8 encoding clone

Standard PCR techniques are used to amplify a CTLA-8 gene sequence from a genomic or cDNA library, or from mRNA. Appropriate primers are selected from the sequences described, and a full length clone is isolated. Various combinations of primers, of various lengths and possibly with differences in sequence, may be prepared. The full length clone can be used as a hybridization probe to screen for other homologous genes using stringent or less stringent hybridization conditions.

In another method, oligonucleotides are used to screen a library. In combination with polymerase chain reaction (PCR) techniques, synthetic oligonucleotides in appropriate orientations are used as primers to select correct clones from a library.

III. Isolation of a human CTLA-8

A human genomic library was obtained from Clontech (Cat. HL1006d) and screened with a cDNA probe composed of a 453 base pair entire coding sequence of a murine CTLA-8. A number of independent lambda clones were found to hybridize strongly with the murine CTLA-8 probe. One clone contained a hybridizing XbaI fragment of approximately 2000 base pairs which corresponded to a fragment previously detected using a similar probe on a human genomic DNA Southern blot. This 2000 base pair fragment was subcloned into Bluescript (Stratagene) and sequenced. This revealed a 240 base pair region 83.8% homologous to the murine CTLA-8. Translation of this region yielded an amino acid sequence 70.8% homologous to the 79 carboxy-terminal amino acids of the murine CTLA-8 putative protein. The exon was used as a probe to screen a library of cDNA made with a primer corresponding to the last 21 nucleotides of the coding region. Three independent cDNA clones were obtained containing the complete coding region of the human CTLA-8. The 468 base pair open reading frame encodes a 155 amino acid polypeptide with a theoretical molecular weight of 17,100 daltons. This human CTLA-8 is 66.4% homologous to the ORF-13 of the virus, and 58.3% homologous to murine CTLA-8 encoded protein. Moreover, the 6 cysteines are conserved between the three genes, as well as the putative glycosylation and phosphorylation sites.

Analysis of the human CTLA-8 amino acid sequence exhibits a hydrophobic stretch of 19 residues, from 7 to about 25, at the amino terminus, similar to a signal peptide. It is highly likely that the human CTLA-8 is a secreted protein of a molecular weight resembling a cytokine. See U.S. Ser. No. 08/077,203.

IV. Biochemical Characterization of CTLA-8 proteins

Two forms of human CTLA-8 were expressed in heterologous cells; the native form, and a recombinant form displaying the FLAG peptide at the carboxy terminus. See, e.g., Crowe et al. (1992) *QIAexDress: The High Level Expression and Protein Purification System* QIAGEN, Inc. Chatsworth, Calif.; and Hopp, et al. (1988) *Bio/Technology* 6:1204–1210. These two forms of the human CTLA-8 protein were introduced into the expression vectors pME18S or pEE12, and subsequently transfected into COS-7 or NS0 cells, respectively, by electroporation. Electroporated cells were then cultivated for 48 hours in RPMI medium supplemented with 10% Fetal Calf Serum. Cells were then incubated with $^{35}$S-Met and $^{35}$S-Cys in order to label cellular proteins. Comparison of the proteins under reducing conditions on SDS-PAGE showed that cells transfected with human CTLA-8 secreted a polypeptide of 15,000 daltons. Non-reducing SDS-PAGE revealed 2 specific bands around 28,000 daltons and 33,000 daltons. Treatment with endoglycosidase F (Boehringer Mannheim) demonstrated that the higher molecular weight species represents an N-glycosylated form of human CTLA-8.

In order to determine if the natural form of human CTLA-8 produced by activated CD4+ T cells was also secreted as a dimer similar to transfected COS-7 and NS0 cells, peripheral blood mononuclear cells (PBMC) were purified from 500 ml of human blood on a Ficoll gradient. B cells, CD8+ T cells, monocytes, and NK cells were depleted using 100 μl of ascitic fluid containing anti-CD19, anti-CD8, anti-CD14, and 25 μg of NKH1 monoclonal antibody (Coulter, Hialeah, Fla.). After 30 minutes of incubation at 40° C., the PBMC were washed twice in RPMI containing 10% Fetal Calf Serum (FCS). Paramagnetic beads coated with goat antibodies to mouse IgG (Dynabeads M450, Dynal, Oslo, Norway) were added at a final concentration of 5 beads/cell to be depleted. Unwanted cells were subsequently removed by 3 passages on a magnet. The remaining cells were CD4+ cells at 87% purity which were diluted to $10^7$ cells/ml in DMEM F12 (Gibco, Gaithersburg, Md.) containing 10% FCS, 10 ng/ml PMA (Sigma, St. Louis, Mo.) and 500 ng/ml ionomycin (Sigma, St. Louis, Mo.). After incubation for 4 hours at 37° C. in 5% $CO_2$, the medium was changed to methionine and cysteine free DMEM (ICN Biomedicals, Costa Mesa, Calif.), supplemented with 1% dialyzed FCS, 10 ng/ml PMA and 500 ng/ml ionomycin, and incubated for 1 hour at 37° C. in 5% $CO_2$. 100 μCi/ml of $^{35}$S-methionine and 35S-cysteine (Amersham) was added, and metabolic labeling was carried out for 18 hours at 37° C. in 5% $CO_2$. Following preclearing of the supernatants with anti-IFN-γ Mab B27 and 0.5 ml of Protein-G Sepharose (Sigma St. Louis, Mo.), the supernatants were immunoprecipitated using monoclonal antibodies to human CTLA-8. Immunoprecipitated proteins were analyzed on SDS-PAGE. CD4+ T cells and transfected NS0 cells reveal two bands at 28,000 and 33,000 daltons corresponding respectively to non N-glycosylated and N-glycosylated forms of human CTLA-8 dimers. Therefore, human CTLA-8 derived from transfected NS0 cells and CTLA-8 isolated from activated T cells display the same biological characteristics.

V. Large Scale Production of Human CTLA-8

For biological assays, human CTLA-8 and human CTLA-8-FLAG were produced in large amounts with transfected COS-7 cells grown in RPMI medium supplemented with 1% Nutridoma HU (Boehringer Mannheim, Mannheim, Germany) and subsequently purified.

In order to produce larger quantities of native human CTLA-8 or human CTLA-8-FLAG, stable transformants of NS0 cells were prepared according to the methodology developed by Celltech (Slough, Berkshire, UK; International Patent Applications WO86/05807, WO87/04462, WO89/01036, and WO89/10404). Both CTLA-8 and CTLA-8-FLAG were subcloned into pEE12 and subsequently transfected into NS0 calls by electroporation. Transfected NS0 cells were seeded in selective glutamine-free DMEM supplemented with 10% Fetal Calf Serum as described in Celltech's protocol. Supernatants from the best producing lines were used in biological assays and purification of human CTLA-8 and human CTLA-8-FLAG.

Purification of Human CTLA-8 protein

Typically, 1 liter of supernatant containing human CTLA-8 or CTLA-8-FLAG was passed on a 60 ml column of $Zn^{++}$ ions grafted to a Chelating Sepharose Fast Flow matrix (Pharmacia, Upsalla, Sweden). After washing with 10 volumes of binding buffer (His-Bind Buffer kit, Novagen, Madison, Wis.), the proteins retained by the metal ions were eluted with a gradient of 20–100 mM Imidazole. The content of human CTLA-8-FLAG in the eluted fractions was determined by dot blot using the anti-FLAG monoclonal antibody M2 (Eastman Kodak, New Haven, Conn.), whereas the content of human CTLA-8 was assessed by silver staining of non-reducing SDS-PAGE. The CTLA-8 containing fractions were then pooled and dialyzed against PBS, and were either used in biological assays or further purified by anion exchange HPLC on a DEAE column. A third step of gel filtration chromatograph was performed on a SUPERDEX G-75 HRD30 column (Pharmacia Uppsala, Sweden) and yielded practically pure human CTLA-8 as analyzed by silver stained SDS-PAGE.

Preparation of antibodies specific for CTLA-8

Inbred Balb/c mice were immunized intraperitoneally with 1 ml of purified human CTLA-8-FLAG emulsified in Freund's complete adjuvant on day 0, and in Freund's incomplete adjuvant on days 15 and 22. The mice were boosted with 0.5 ml of purified human CTLA-8-8 administered intravenously.

Hybridomas were created using the non-secreting myeloma cells line SP2/0-Ag8 and polyethylene glycol 1000 (Sigma, St. Louis, Mo.) as the fusing agent. Hybridoma cells were placed in a 96-well Falcon tissue culture plate (Becton Dickinson, NJ) and fed with DMEM F12 (Giboo, Gaithersburg, Md.) supplemented with 80 μ/ml gentamycin, 2 mM glutamine, 10% horse serum (Gibco, Gaithersburg, Md.), 1% ADCM (CRTS, Lyon, France) $10^{-5}$ M azaserine (Sigma, St. Louis, Mo.) and $5 \times 10^{-5}$ M hypoxanthine. Hybridoma supernatants were screened for antibody production against human CTLA-8 by immunocytochemistry (ICC) using acetone fixed human CTLA-8 transfected COS-7 cells and by ELISA using human CTLA-8-FLAG purified from COS-7 supernatants as a coating antigen. Aliquots of positive cell clones were expanded for 6 days and cryopreserved as well as propagated in ascites from pristane (2,6,10,14-tetramethylpentadecane, Sigma, St. Louis, Mo.) treated Balb/c mice who had received on intraperitoneal injection of pristane 15 days before. About $10^5$ hybridoma cells in 1 ml of PBS were given intraperitoneally, and 10 days later, ascites were collected from each mouse.

After centrifugation of the ascites, the antibody fraction was isolated by ammonium sulfate precipitation and anion-exchange chromatography on a Zephyr-D silicium column (IBF Sepracor) equilibrated with 20 mM Tris pH 8.0. Proteins were eluted with a NaCl gradient (ranging from 0 to 1 M NaCl). 2 ml fractions were collected and tested by ELISA for the presence of anti-CTLA-8 antibody. The fractions containing specific anti-CTLA-8 activity were pooled, dialyzed, and frozen. Aliquots of the purified monoclonal antibodies were peroxydase labeled.

Quantification of human CTLA-8

Among the antibodies specific for CTLA-8, Ab25, and peroxidase labeled Ab16 were selected to quantitate levels of human CTLA-8 using a sandwich assay. Purified Ab25 was diluted at 2 µg/ml in coating buffer (carbonate buffer, pH 9.6. 15 mM $Na_2CO_3$, 35 mM $NaHCO_3$). This diluted solution was coated onto the wells of a 96-well ELISA plate (Immunoplate Maxisorp F96 certified, NUNC, Denmark) overnight at room temperature. The plates were then washed manually one with a washing buffer consisting of Phosphate Buffered Saline and 0.05% Tween 20 (Technicon Diagnostics, USA). 110 µl of purified human CTLA-8 diluted in TBS-B-T buffer [20 mM Tris, 150 mM NaCl, 1% BSA (Sigma, St. Louis, Mo.), and 0.05% Tween 20] was added to each well. After 3 hours of incubation at 37°C., the plates were washed once. 100 µl of peroxidase labeled Ab16 diluted to 5 µg/ml in TBS-B-T buffer was added to each well, and incubated for 2 hours at 37° C. The wells were then washed three times in washing buffer. 100 µl of peroxidase substrate, 2.2' Azino-bis(3 ethylbenzthiazoine-6-sulfonic acid) (ABTS), diluted to 1 mg/ml in citrate/phosphate buffer, was added to each well, and the colorimetric reaction was read at 405 nm. The lowest concentration of human CTLA-8 detected was 0.015 ng/ml.

V. Induction of IL-6 secretion by treatment of various cell types with CTLA-8

Kidney epithelial carcinoma cell lines (TUMT and CHA) were also cultured in complete RPMI 1640 medium (Gibco BRL, Grand Island, N.Y.), supplemented with 2 mM L-glutamine, 100 U/ml penicillin, 50 µg/ml gentamycin, 20 mM Hepes buffer and heat-inactivated 10% FCS. Cells ($10^4$ cells/well) were incubated in 96-well plates (Falcon) in a final volume of 250 µl of complete culture medium. Increasing concentrations of human CTLA-8 were added at the onset of the culture. Cell-free supernatants were collected after 48 hours, and stored at −20° C. until cytokine assays. IL-6 levels were measured by two-site sandwich ELISA as described in Abrams, et al. (1992) *Immunol. Rev.* 127:5–24. Both cell lines exhibited dose dependent increases in IL-6 secretion with increasing concentrations of CTLA-8. In view of these results, other cell lines will also be screened for responses to other species of CTLA-8 variants.

MRC-5 human lung fibroblasts were obtained from the ATCC (Rockville, Md.) and were cultured in complete RPMI 1640 medium (Gibco BRL, Grand Island, N.Y.), supplemented with 2 nM L-glutamine, 100 U/ml penicillin, 50 mg/ml gentamycin, 20 mM Hepes buffer and heat-inactivated 10% FCS. Cells ($10^4$ cells/well) were incubated in 96-well plates (Falcon) in a final volume of 250 µl of complete culture medium. Increasing concentrations of human CTLA-8-8 was added at the onset of the culture. Cell-free supernatants were collected after 48 hours, and stored at −20° C. until cytokine assays. IL-6 levels were measured by ELISA. Dose dependent induction of IL-6 was observed.

Similar results were obtained using adult and child dermal fibroblasts, human brain epithelial cells, and human bronchus epithelial cells. Kidney mesangium cells should respond similarly.

VI. CTLA-8 effect on hematopoiesis

Human CD34+ precursor cells were obtained from cord blood collected during normal deliveries. Light density mononuclear cells were enriched on a Ficoll-Hypaque gradient. Cells bearing the CD34 antigen were subsequently isolated by positive selection as described in, e.g., Saeland, et al. (1988) *Blood* 72:1580–1588, except for the panning step, which was replaced by anti-CD34 mAb coupled to MACS magnetic microbeads and a mini-MACS magnet (Miltenyi Biotec, Inc. Sunnyvale, Calif.).

Rheumatoid synoviocytes were seeded in 96 well plates in RPMI 1640 medium supplemented with 10% FCS at a density of 10,000 cell per well. After one day of culture at 37° C., 5% $CO_2$, these cells were irradiated at 4000 rads. Purified hCTLA-8 or the corresponding protein control were then added at a final concentration of 100 ng/ml. Purified CD34+ cells were added at the same time and co-cultured until day 21.

Following 8 to 21 days of co-culture, hCTLA-8 significantly increased the proliferation and differentiation of CD34+ into neutrophils. May-Grünwald-Giemsa staining revealed the appearance of polymorphonuclear cells typical of neutrophils. FACS analysis of these cells also showed surface antigen expression consistent with a neutrophil phenotype, i.e., CD14, CD15, CD16, and CD33. Monocyte-like cells were also detected as shown by May-Grünwald-Giemsa staining, and by the presence of CD14+ cells by FACS analysis VII. CTLA-8 induces the secretion of G-CSF Synoviocytes from patients with rheumatoid arthritis and kidney carcinoma cells ($10^4$ cells/well) were incubated with increasing concentrations of human CTLA-8. After 48 hours, concentrations of G-CSF were measured by standard ELISA techniques (R and D Systems). Secretion of G-CSF was increased significantly in both types of cells. As such, part of the effects of CTLA-8 may also operate through the mechanism of G-CSF induction, though the kinetics of effects may be different.

VIII. In vivo activity of CTLA-8

Recombinant, purified, endotoxin-free murine CTLA-8 was administered subcutaneously to normal C57BL/6 mice at a concentration of 10 µg per mouse every day for three days. Blood parameters were evaluated each day. A dose dependent rise in peripheral blood neutrophils was observed in the CTLA-8 treated animals.

Protection from bacterial challenge

A lyophilized pathogenic human *E. coli* isolate (American Type Culture Collection, Batch Number 93-10SV) was reconstituted in 1 ml of sterile LB broth. A 1:10 dilution was cultured overnight at 37° C., diluted 1:20, and cultured for hours to yield log phase bacterial growth. The culture was then centrifuged at 2000 rpm for 10 min and the pellet resuspended in freezing media, i.e., PBS with 10% glycerol. The culture was aliquoted into cryogenic vials and flash frozen. One vial was thawed, diluted 1:10, and plated for a bacterial titer, measured in colony forming units (CFU). The bacteria was further titrated in normal C57BL6/N mice to determine the lethal dose (LD).

The protective ability of CTLA-8 was assessed by pretreatment with 10 µg of CTLA-8, followed by intraperitoneal injection of $2\times10^7$ CFU of bacteria three hours later. The mice were sacrificed 18 hours later and equal portions of the livers were removed, pooled, and homogenized in 10 ml of sterile PBS. The homogenates were diluted $10^{-1}$ to $10^{-7}$ and then plated, in duplicate, on LB agar plates. Following overnight incubation at 37° C., bacterial counts were assessed. CTLA-8 pretreated mice gave 2–3 orders of magnitude lower bacterial counts than untreated control animals. In parallel, a second group of mice were treated as above and mortality measured. Varying concentrations of CTLA-8 were also assessed, i.e., at 1 µg, 5 µg, and 10 µg. A dose-dependent protective effect against lethal bacterial infection was observed in mice treated with CTLA-8.

Peripheral Blood Transfer

5 µg of CTLA-8 was injected into one set of C57BL6/N mice every day for seven days. Similarly, another set of mice was treated with G-CSF. On day 7, separated white blood cells from the treated mice were transferred to irradiated recipients. On day 8 spleens were harvested for CFU-s assay. Additional cells were plated in CFU-c assays. See, Johnson, et al. *Proc. Nat'l. Acad. Sci.* 74:3879–3884. The two assays allow for a determination if CTLA-8 mobilizes bone marrow progenitor cells in the same pathway as G-CSF. See Table 1. 5 µg of CTLA-8 was injected into one set of C57BL6/N mice every day for seven days. Similarly, another set of mice was treated with G-CSF. On day 7, separated white blood cells from the treated mice were transferred to irradiated recipients. On day 8 spleens were harvested for CFU-s assay, and on day 12 white blood cells collected for CFU-c assay. Both assays are described in Johnson, et al. (1977) *Proc. Nat'l. Acad. Sci.* 74:3879–3884. There appears to be no dramatic effect detected in these assays, though the neutrophil counts are increased.

TABLE 1

Effect of CTLA-8 or G-CSF on hematopoietic progenitor cells

| factor | CFU-s | CFU-c |
|---|---|---|
| PBS | 6 | 1.3 |
| CTLA-8 | 3 | 3.7 |
| G-CSF | 13 | 8.0 |

IX. Antiviral activity of CTLA-8

Standard techniques in virology and tissue culture can be used to determine the antiviral activity of CTLA-8. See Harper (ed.) (1993) *Virology LabFax,* Academic Press, NY; and Fields, et al. (eds.) (1986) *Fundamental Virology,* Raven Press, NY. Appropriate tissue culture cells are infected with a suitable amount (plaque forming units, pfu) of virus stock. CTLA-8 is added at various times after infection, and a plaque assay performed to determine viral load reduction.

Alternatively, an appropriate animal viral model is injected with an effective dose of CTLA-8 over a period of days. Levels of viral infection are determined as described above. Levels of IFN-β are also assayed by standard ELISA techniques.

X. Isolating CTLA-8 Homologues

The binding composition is used for screening of an expression library made from a cell line which expresses a CTLA-8 protein. Standard staining techniques are used to detect or sort intracellular or surface expressed antigen, or surface expressing transformed cells are screened by panning.

Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at 2–3×10$^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of huIL-10-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 µl/ml of 1 M NaN$_3$ for 20 min. Cells are then washed with HBSS/saponin 1×. Soluble antibody is added to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and pre-incubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85–90° C.

Alternatively, the binding compositions are used to affinity purify or sort out cells expressing the antigen. See, e.g., Sambrook, et al. or Ausubel, et al.

Similar methods are applicable to isolate either species or allelic variants. Species variants are isolated using cross-species hybridization techniques based upon a full length isolate or fragment from one species as a probe, or appropriate species.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A composition comprising a substantially pure combination of:
    a) mammalian G-CSF and CTLA-8; or
    b) mammalian G-CSF CTLA-8, and IL-6.
2. The composition of claim 1, wherein said mammalian G-CSF is human G-CSF.
3. The composition of claim 1, wherein said combination is G-CSF and CTLA-8.
4. The composition of claim 1, wherein
    a) said mammalian CTLA-8 is human CTLA-8; and/or
    b) said mammalian IL-6 is human IL-6.
5. A composition of claim 1, wherein:
    a) said G-CSF is a recombinant protein;
    b) said CTLA-8 is a recombinant protein; and/or
    c) said IL-6 is a recombinant protein.
6. The composition of claim 5, wherein at least one of said recombinant proteins is made in a mammalian cell or a prokaryotic cell.
7. A composition of claim 1, further comprising a pharmaceutically acceptable carrier.
8. A pharmaceutical composition comprising mammalian G-CSF and mammalian CTLA-8.
9. The pharmaceutical composition of claim 8, further comprising mammalian IL-6, which further attenuates a symptom of sepsis or abnormal hematopoiesis.
10. The pharmaceutical composition of claim 8, consisting essentially of said G-CSF and said CTLA-8.

11. The pharmaceutical composition of claim 9, consisting essentially of said G-CSF, said CTLA-8, and said IL-6.

12. The pharmaceutical composition of claim 10, further comprising a pharmaceutically acceptable carrier.

13. The pharmaceutical composition of claim 11, further comprising a pharmaceutically acceptable carrier.

14. The pharmaceutical composition of claim 8, which attenuates symptoms resulting from a microbial infection.

15. The pharmaceutical composition of claim 9, which attenuates symptoms resulting from a microbial infection.

* * * * *